United States Patent [19]

Mikami et al.

[11] Patent Number: 5,434,289
[45] Date of Patent: Jul. 18, 1995

[54] PROCESS FOR PRODUCING OPTICALLY ACTIVE β-HYDROXYKETONE

[75] Inventors: Koichi Mikami; Satoru Matsukawa; Masaki Shimizu; Masahiro Terada, all of Tokyo; Noboru Sayo, Kanagawa, all of Japan

[73] Assignee: Takasago International Corporation, Tokyo, Japan

[21] Appl. No.: 208,379

[22] Filed: Mar. 10, 1994

[30] Foreign Application Priority Data

Mar. 11, 1993 [JP] Japan .................................. 5-076391

[51] Int. Cl.⁶ .................... C07C 327/00; C07C 69/76; C07C 45/00
[52] U.S. Cl. ....................... 558/252; 560/55; 560/145; 560/179; 560/184; 560/185; 568/315; 568/317; 568/391; 568/394; 568/395
[58] Field of Search ............... 568/308, 315, 317, 391, 568/394, 395; 558/252; 560/55, 145, 179, 184, 185

[56] References Cited

PUBLICATIONS

Chemistry Letters, (1990) pp. 1015–1018.
Synlett (Jun. 1991), pp. 439–440.
Tetrahedron Letters, vol. 33, No. 13, pp. 1729–1732 (1992).
J. Am. Chem. Soc. 1992, 114, pp. 4418–4420.
Chemistry and Industry, 1 Dec. 1986, p. 824.
J. Am. Chem. Soc. 1991, 113, pp. 9365–9366.
J. Am. Chem. Soc., 1993, 115, pp. 7039–7040.

*Primary Examiner*—Alan Siegel
*Attorney, Agent, or Firm*—Sughrue, Mion, Zinn, Macpeak & Seas

[57] ABSTRACT

A process for producing an optically active β-hydroxyketone represented by formula (I):

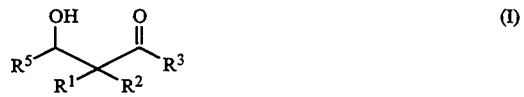

by catalytic asymmetrical aldol reaction is disclosed, comprising reacting a silyl-enol ether represented by formula (II):

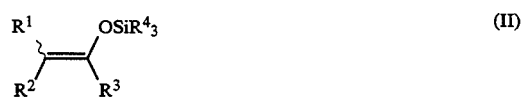

with a substituted aldehyde represented by formula (III):

$$R^5CHO \quad \quad (III)$$

in the presence of a binaphthol-titanium complex represented by formula (IV):

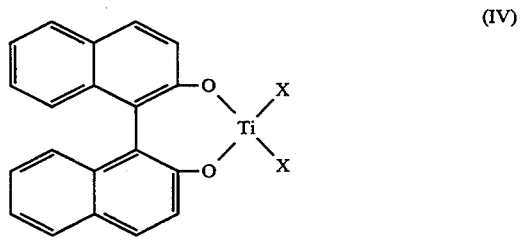

An optically active β-hydroxyketone is efficiently produced with diastereo-specificity and enantio-specificity.

6 Claims, No Drawings

PROCESS FOR PRODUCING OPTICALLY ACTIVE β-HYDROXYKETONE

FIELD OF THE INVENTION

This invention relates to a process for producing an optically active β-hydroxyketone of formula (I) shown below by an asymmetrical aldol reaction in the presence of a catalyst. The optically active β-hydroxyketone is useful, for example, as an intermediate for biologically active substances in the medical and pharmaceutical fields, since it has a plurality of functional groups.

BACKGROUND OF THE INVENTION

Known processes for preparing an optically active β-hydroxyketone (an optically active alcohol) through a catalytic asymmetrical aldol reaction include (1) reaction between an aldehyde and a silyl-enol ether in the presence of a binaphthol-oxotitanium complex (see T. Mukaiyama, et al., *Chem. Letter.*, pp. 1015–1018 (1990)), (2) reaction between an aldehyde and a silyl-enol ether in the presence of a boron complex derived from tartaric acid (see K. Furuta, et al., *Syn. Lett.*, pp. 439–440 (1991)), (3) reaction between an aldehyde and a silyl-enol ether in the presence of a boron complex derived from menthone (see E. R. Parmee, et al., *Tetrahedron Lett.*, Vol. 33, pp. 1729–1732 (1992)), and (4) reaction between an aldehyde and nitromethane in the presence of a binaphthol lanthanoid complex (see H. Sakai et al., *J. Am. Chem. Soc.*, Vol. 114, pp. 4418–4420 (1992)). However, these conventional processes were unsatisfactory in terms of catalytic activity and optical purity (diastereo-selectivity or enantio-selectivity). Besides, preparation of the above-mentioned complex catalysts involves complicated operation.

SUMMARY OF THE INVENTION

As a result of extensive investigations, the present inventors have found that an optically active β-hydroxyketone can be obtained efficiently with high diastereoselectivity and high enantio-selectivity by using an optically active binaphthol-titanium complex. The present invention has been completed based on this finding.

The present invention relates to a process for producing an optically active β-hydroxyketone represented by formula (I):

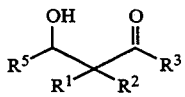
(I)

wherein $R^1$ and $R^2$, which may be the same or different, each represent a hydrogen atom or a lower alkyl group; $R^3$ represents a lower alkyl group, a lower alkyloxy group, a phenyloxy group or a lower alkylthio group; and $R^5$ represents an alkyl group having from 1 to 10 carbon atoms, a halogenated lower alkyl group, a lower alkenyl group, a benzyloxymethyl group or a lower alkyloxycarbonyl group, comprising reacting a silyl-enol ether represented by formula (II):

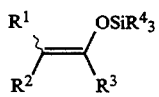
(II)

wherein $R^1$, $R^2$, and $R^3$ are as defined above; and three $R^4$s, which may be the same or different, each represent a lower alkyl group or a phenyl group, with a substituted aldehyde represented by formula (III):

$$R^5CHO \qquad (III)$$

wherein $R^5$ is as defined above, in the presence of a binaphthol-titanium complex represented by formula (IV):

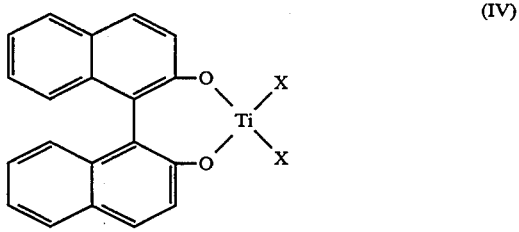
(IV)

wherein X represents a chlorine atom or a bromine atom.

DETAILED DESCRIPTION OF THE INVENTION

In formulae (I), (II), and (III), the terminology "lower" means from 1 to 5 carbon atoms forming a straight or branched carbon chain.

The silyl group (—SiR$^4$$_3$) in formula (II) includes a trimethylsilyl group, a triethylsilyl group, a tri-n-propylsilyl group, a tri-n-butylsilyl group, a tri-n-pentylsilyl group, a t-butyldimethylsilyl group, a triisopropylsilyl group, a dimethylisopropylsilyl group, a phenyldimethylsilyl group, and a triphenylsilyl group.

To take an instance, specific examples of the silyl-enol ether of formula (II) wherein the silyl group is a trimethylsilyl group are methyl propionate-(E)-trimethylsilyl-enol ether, methyl propionate-(Z)-trimethylsilyl-enol ether, isopropyl propionate-(E)-trimethylsilyl-enol ether, isopropyl propionate-(Z)-trimethylsilyl-enol ether, phenyl propionate-(E)-trimethylsilyl-enol ether, phenyl propionate-(Z)-trimethylsilyl-enol ether, phenyl isobutyrate-trimethylsilyl-enol ether, 3-pentanone-(E)-trimethylsilyl-enol ether, 3-pentanone-(Z)-trimethylsilyl-enol ether, 2-pentanonetrimethylsilyl-enol ether, propiophenone-(E)-trimethylsilyl-enol ether, propiophenone-(Z)-trimethylsilyl-enol ether, t-butyl thiopropionate-(E)-trimethylsilyl-enol ether, t-butyl thiopropionate-(Z)-trimethylsilyl-enol ether, ethyl thiopropionate-(E)-trimethylsilyl-enol ether, ethyl thiopropionate-(Z)-trimethylsilyl-enol ether, and S-ethyl thioacetate-trimethylsilyl-enol ether.

These silyl-enol ethers are easily synthesized from the corresponding ketones, esters or thioesters in accordance with the processes described in E. W. Colvin, *Silicon in Organic Synthesis*, pp. 198–287, Butterworths, London (1981) and N. Slougui, et al., *Synthesis*, p. 58 (January 1982).

The following process may be mentioned as an instance of general synthesis of the silyl-enol ether. A dialkylamine is dissolved in tetrahydrofuran. The solution is cooled to about 0° C., and a solution of n-butyl lithium in tetrahydrofuran, etc. is added thereto dropwise to prepare a lithium dialkylamide solution. The solution is cooled to about −78° C., and a ketone, an ester or a thioester is added to the solution dropwise. After about 30 minutes, a silyl chloride derivative is added thereto, followed by allowing the mixture to sufficiently react at that temperature. After the reaction, the salt formed is removed by filtration. The separated salt and the reaction container are washed with pentane, and the washing is combined with the filtrate. The combined solution is distilled to remove pentane, and the residue is further distilled to obtain a desired silyl-enol ether.

Specific examples of the substituted aldehyde represented by formula (III) include acetaldehyde, chloroacetaldehyde, ethanal, propanal, butanal, pentanal, hexanal, heptanal, octylaldehyde, nonylaldehyde, methoxymethylaldehyde, ethoxymethylaldehyde, crotonaldehyde, benzyloxymethylaldehyde, methyl glyoxylate, ethyl glyoxylate, isopropyl glyoxylate, n-butyl glyoxylate, and t-butyl glyoxylate. The glyoxylic esters can be prepared by, for example, the process of T. Ross Kelly, et al. (see *Synthesis*, pp. 544–545 (1972)).

The optically active binaphthol-titanium complex represented by formula (IV) which can be used as a catalyst in the present invention can be prepared by, for example, the process disclosed in JP-A-2-40344 (the term "JP-A" as used herein means an "unexamined published Japanese patent application"). In more detail, a titanium tetrahalide (halogen: chlorine or bromine) and titanium tetraisopropoxide are mixed in hexane to prepare titanium dihalogenodiisopropoxide crystals, which are then dissolved in toluene. Separately, at least 0.5 g, per mmol of the substrate, of Molecular Sieve 4A powder (a commercially available product) is added to methylene chloride. The above-prepared titanium dihalogenodiisopropoxide toluene solution and then binaphthol were successively added thereto, followed by stirring for about 1 hour to obtain a binaphthol-titanium complex (IV).

The binaphthol-titanium complex (IV) takes an (R)-form when synthesized from (R)-binaphthol or an (S)-form when synthesized from (S)-binaphthol. A choice of the isomeric form is made according to the absolute configuration of a desired optically active β-hydroxyketone (I). That is, the use of (R)-binaphthol provides an optically active β-hydroxyketone (I) having (R) configuration with respect to the hydroxyl group.

In carrying out the present invention, it is preferred that a silyl-enol ether (II) and an almost equimolar amount of a substituted aldehyde (III) are added to a solution of a binaphthol-titanium complex (IV) in an organic solvent and allowed to react. It is preferred that the respective concentrations of the silyl-enol ether (II) and the substituted aldehyde (III) in the organic solvent are approximately from 0.1 to 5 mol/l.

Usable organic solvents include halogenated hydrocarbons, e.g., methylene chloride, chloroform, and carbon tetrachloride; aromatic hydrocarbons, e.g., benzene and toluene; aprotic solvents, e.g., tetrahydrofuran, diethyl ether, and dimethoxyethane; acetonitrile, propionitrile, butyronitrile, nitromethane, and nitroethane. Among them, methylene chloride and toluene are preferred.

For obtaining a product in high optical yield, the binaphthol-titanium complex (IV) is preferably used in an amount of approximately from 0.02 to 1 mol, and more preferably approximately from 0.05 to 0.1 mol, per mol of the respective amounts of the silyl-enol ether (II) and the substituted aldehyde (III), i.e., per mol of the amount of the silyl-enol ether (II) and per mol of the amount of the substituted aldehyde (III).

The preferred reaction temperature is approximately from $-50°$ to $0°$ C., and particularly preferred reaction temperature is approximately from $-30°$ to $-10°$ C. The preferred reaction time is approximately from 3 to 20 hours.

After completion of the reaction, an alkali, e.g., a sodium hydrogencarbonate aqueous solution, is added to the reaction mixture, and the mixture is extracted with a solvent, e.g., diethyl ether or ethyl acetate. After drying, the solvent of the extract is evaporated, and the residue is purified by column chromatography on silica gel, etc., to obtain a desired optically active β-hydroxyketone (I) in high yield.

Alternatively, an aqueous solution of an alkali, e.g., sodium hydrogencarbonate, is added to the reaction mixture at $0°$ C., and the mixture is extracted with a water-immiscible organic solvent, such as diethyl ether or ethyl acetate. The extract is distilled under reduced pressure to remove the solvent to give a silyl-enol ether as an intermediate. In using a substituted aldehyde (III) wherein $R^5$ is an alkyl group, the intermediate is represented by formula (I'):

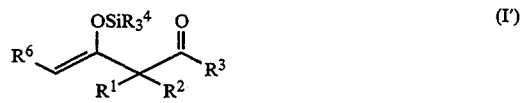

wherein $R^1$, $R^2$, $R^3$, and $R^4$ are as defined above; and $R^6$ represents a hydrogen atom or an alkyl group. In using a substituted aldehyde (III) wherein $R^5$ is a benzyloxymethyl group or an alkyloxycarbonyl group, the intermediate is represented by formula (I''):

wherein $R^1$, $R^2$, $R^3$, $R^4$, and $R^5$ are as defined above.

The resulting silyl-enol ether intermediate (I') or (I'') is dissolved in methanol at $0°$ C., and a small amount of a methanol solution of hydrochloric acid is added to the solution at $0°$ C. The solvent is removed by distillation. Purification by silica gel column chromatography gives a desired optically active β-hydroxyketone (I) in high yield. The present invention will now be illustrated in greater detail with reference to Examples, but the present invention should not be construed as being limited thereto. All the percents are by weight unless otherwise indicated.

Analyses in Examples were conducted by means of the following instruments or under the following conditions.

$^1$H-NMR: GEMINI 300 (300 MHz), manufactured by VARIAN Co., Ltd.
$^{13}$C-NMR: GEMINI 300 (75 MHz), manufactured by VARIAN Co., Ltd.
Optical Rotation:
  Polarimeter DIP-370, manufactured by JEOL Ltd.
High Performance Liquid Chromatography (HPLC):
  Daicel chiral OB column (hexane/isopropyl alcohol=20/1 by volume; flow rate: 0.9 ml/min; detection UV)

The syn-anti ratio was decided from the integrated value of NMR in accordance with the method of J. Canceill, et al., *Bull. Soc. Chim. Fr.*, pp. 1024–1030

(1967) and *Topics in Stereochemistry*, Vol. 13, p. 1, John Wiley & Sons, Inc. (1982).

The enantiomer excess (% ee) was determined by $^1$H-NMR analysis on the α-methoxy-α-trifluoromethylphenylacetic acid ester of the product obtained in accordance with the process of D. Parker, et al., *Chem. Rev.*, Vol. 91, pp. 1441–1457 (1991) or the process of J. A. Dale, et al., *J. Org. Chem.*, Vol. 34, pp. 2543–2549 (1969). The method described in Example 2 below was used in the following Examples.

EXAMPLE 1

In a 50 ml Schlenk flask purged with argon were charged 2.98 ml (10 mmol) of titanium tetraisopropoxide and 5 ml of hexane, and 1.10 ml (10 mmol) of titanium tetrachloride was added thereto. The mixture was stirred at room temperature for 10 minutes, followed by allowing to stand at room temperature for 3 hours whereupon white crystals precipitated. The solvent was withdrawn by means of a syringe, and the crystals were recrystallized from 5 ml of hexane. Removal of the solvent and subsequent recrystallization were repeated twice. Drying under reduced pressure gave 3.09 g of white titanium dichlorodiisopropoxide. The product was dissolved in 43 ml of toluene to prepare a 0.3 mol/l solution.

Separately, 0.5 g of Molecular Sieve 4A powder (a product of Aldrich Co.) was put in a 25 ml flask. After purging with argon, 3 ml of toluene was added to the flask. Thereafter, 6.7 ml (2 mmol) of the above-prepared toluene solution of titanium dichlorodiisopropoxide and 573 mg (2 mmol) of (R)-binaphthol were added thereto, followed by stirring at room temperature for 1 hour to obtain an (R)-binaphthol-titanium complex (hereinafter designated (R)-1).

0.5 ml (0.1 mmol) of the resulting solution was cooled to 0° C. in an ice bath, and 157 mg (1 mmol) of (Z)-3-trimethylsilyloxy-2-pentene (86% Z) was added thereto. To the mixture were added 130 mg (1 mmol) of freshly distilled n-butyl glyoxylate and 0.5 ml of methylene chloride, and the system was allowed to react at 0° C. for 0.5 hour.

The reaction mixture was poured into 10% hydrochloric acid-methanol cooled to 0° C. The solution was filtered through Celite, and the filtrate was extracted three times with a 5 ml portion of diethyl ether. The organic layer combined was washed with a saturated sodium chloride aqueous solution and dried over magnesium sulfate. The solvent was removed by distillation, and the residue was purified by silica gel column chromatography (eluent: hexane/ethyl acetate=15/1 by volume) to obtain 135 mg (yield 63%) of n-butyl 2-hydroxy-3-methyl-4-oxohexanonate. $[α]_D^{26}$: +5.0° (c=1.0, CHCl$_3$) (98% syn; 99% ee) IR (neat): 3500, 2970, 1730, 1460, 1260, 760 cm$^{-1}$ Syn-isomer: $^1$H-NMR (CDCl$_3$) δ: 0.94 (t, J=7.4 Hz, 3H), 1.07 (t, J=7.0 Hz, 3H), 1.15 (d, J=7.3 Hz, 3H), 1.38 (m, 2H), 1.65 (m, 2H), 2.56 (q, J=7.0 Hz, 2H), 2.94 (dq, J=3.9, 7.4 Hz, 1H), 3.12 (d, J=4.6 Hz, 1H), 4.20 (d, J=6.7 Hz, 2H), 4.56 (dd, J=3.9, 4.6 Hz, 1H) $^{13}$C-NMR (CDCl$_3$) δ: 7.6, 10.8, 13.7, 19.1, 30.6, 34.2, 49.2, 65.9, 71.2, 173.5, 211.8

Anti-isomer: $^1$H-NMR (CDCl$_3$) δ: 3.04 (m, 1H), 3.30 (d, J=7.6 Hz) $^{13}$C-NMR (CDCl$_3$) δ: 7.5, 13.1, 15.3, 19.0, 30.5, 34.8, 49.1, 65.6, 72.8, 173.5, 211.7

EXAMPLE 2

(1) syn-Butyl 2-Hydroxy-3-methyl-4-(trimethylsilyl)oxy-4-hexenoate (intermediate)

To a solution of 21.6 mg (0.05 mmol) of a chiral titanium complex, (R)-1, in 3 ml of methylene chloride were added 157 mg (1 mmol) of Z-3-(trimethylsilyl)oxy-2-pentene and subsequently a solution of 130 mg (1 mmol) of freshly distilled butyl glyoxylate in 0.5 ml of methylene chloride at 0° C. After stirring for 30 minutes at that temperature, the resultant mixture was poured into 10 ml of a saturated sodium hydrogencarbonate aqueous solution at 0° C. The solution was filtered through a pad of Celite, and the filtrate was extracted three times with a 5 ml portion of diethyl ether. The combined organic layer was washed with brine, dried over magnesium sulfate and evaporated under reduced pressure. Separation by silica gel chromatography (eluent: hexane/ethyl acetate=15/1 by volume) gave 181 mg (0.63 mmol; yield 63%) of butyl 2-hydroxy-3-methyl-4-(trimethylsilyl)oxy-4-hexenoate.

IR (neat): 3510, 2960, 1730, 1460, 1260, 1060, 840, 760 cm$^{-1}$

Z-isomer: $^1$H-NMR (CDCl$_3$) δ: 0.20 (s, 9H), 0.93 (t, J=7.1 Hz, 3H), 0.95 (d, J=7.0 Hz, 3H), 1.37 (m, 2H), 1.55 (d, J=6.7 Hz, 3H), 1.65 (m, 2H), 2.52 (dq, J=2.7, 7.0 Hz, 1H), 2.66 (d, J=5.4 Hz, 1H), 4.18 (t, J=6.6 Hz, 2H), 4.45 (dd, J=2.7, 5.4 Hz, 1H), 4.69 (q, J=6.7 Hz, 1H) $^{13}$C-NMR (CDCl$_3$) δ: 0.7, 11.1, 13.7, 13.7, 19.1, 30.7, 43.4, 65.5, 71.4, 103.5, 151.0, 174.6

E-isomer: $^1$H-NMR (CDCl$_3$) δ: 1.49 (d, J=6.6 Hz, 3H), 4.38 (d, J=4.2 Hz, 1H), 4.55 (q, J=6.6 Hz, 1H) $^{13}$C-NMR (CDCl$_3$) δ: 0.2, 11.7, 14.1, 14.1, 19.3, 30.7, 36.2, 64.6, 72.6, 103.1, 152.2, 174.6

(2) Butyl 2Hydroxy-3-methyl-4-oxohexanoate:

To a solution of 20 to 30 mg of the silyl-enol ether product obtained in (1) above in 2 ml of methanol was added 2 to 3 drops of 10% hydrochloric acid-methanol. After stirring for 5 minutes, the resulting mixture was evaporated under reduced pressure, and the residue was purified by silica gel column chromatography (eluent: hexane/ethyl acetate=10:1 by volume) to obtain the titled compound in a quantitative yield.

$[α]_D^{26}$: +5.0° (c=1.0, CHCl$_3$) (98% syn; 99% ee)
3500, 2970, 1730, 1460, 1260, 760 cm$^{-1}$ HRMS for C$_{11}$H$_{20}$O$_4$: Calcd.: 216.1362; found 216.1368

Syn-isomer: $^1$H-NMR (CDCl$_3$) δ: 0.94 (t, J=7.4 Hz, 3H), 1.07 (t, J=7.0 Hz, 3H), 1.15 (d, J=7.4 Hz, 3H), 1.38 (m, 2H), 1.65 (m, 2H), 2.56 (q, J=7.0 Hz, 2H), 2.94 (dq, J=3.9, 7.4 Hz, 1H), 3.12 (d, J=4.6 Hz, 1H), 4.20 (t, J=6.7 Hz, 2H), 4.56 (dd, J=3.9, 4.6 Hz, 1H) $^{13}$C-NMR (CDCl$_3$) δ: 7.6, 10.8, 13.7, 19.1, 30.6, 34.2, 49.2, 65.9, 71.2, 173.5, 211.8

Anti-isomer: $^1$H-NMR (CDCl$_3$) δ: 3.04 (m, 1H), 3.30 (d, J=7.6 Hz) $^{13}$C-NMR (CDCl$_3$) δ: 7.5, 13.1, 15.3, 19.0, 30.5, 34.8, 49.1, 65.6, 72.8, 173.5, 211.7

(3) Determination of Enantiomer Excess (Optical purity):

The enantiomer excess of the β-hydroxyketones obtained in (2) above was determined by $^1$H-NMR analysis after conversion to the (R)- or (S)-α-methoxy-α-trifluoromethylphenylacetic acid (hereinafter abbreviated as MTPA) ester. To the solution of 10 to 15 mg of the β-hydroxyketone and 0.2 ml of pyridine in 1 ml of methylene chloride was added 2 to 3 drops of the (R)- or (S)-MTPA chloride at room temperature. After the reaction was monitored for completion by TLC, the resultant solution was poured into water. Usual workup followed by short-path column chromatography gave the (R)- or (S)-MTPA ester of the β-hydroxyketone in a quantitative yield.

(R)-MTPA Ester of syn-isomer: $^1$H-NMR (CDCl$_3$) δ: 0.92 (t, J=7.4 Hz, 3H), 0.96 (t, J=7.2 Hz, 3H), 1.15 (d, J=7.3 Hz, 3H), 1.36 (m, 2H), 1.62 (m, 2H), 2.40 (q, J=7.2 Hz, 2H), 3.07 (qd, J=4.4, 7.3 Hz, 1H), 3.63 (s, 3H), 4.20 (t, J=6.6 Hz, 2H), 5.74 (d, J=4.4 Hz, 1H)

(S)-MTPA Ester of syn-isomer: $^1$H-NMR (CDCl$_3$) δ: 0.92 (t, J=7.4 Hz, 3H), 1.06 (t, J=7.2 Hz, 3H), 1.19 (d, J=7.1 Hz, 3H), 1.36 (m, 2H), 1.62 (m, 2H), 2.52 (q, J=7.2 Hz, 2H), 3.13 (qd, J=4.0, 7.1 Hz, 1H), 3.54 (s, 3H), 4.18 (t, J=6.6 Hz, 2H), 5.72 (d, J=4.0 Hz, 1H)

EXAMPLE 3

(1) Butyl 2-Hydroxy-4-(trimethylsilyl)oxy-4-heptanoate (intermediate):

0.5 ml (0.1 mmol) of (R)-1 solution prepared in the same manner as in Example 1 were cooled to 0° C., and 157 mg (1 mmol) of 2-trimethylsilyloxy-1-pentene and subsequently mg (1 mmol) of freshly distilled n-butyl glyoxylate and 0.5 ml of methylene chloride were added thereto, followed by allowing the mixture to react at 0° C. for 0.5 hour. The resulting mixture was poured into 10 ml of a saturated sodium hydrogencarbonate aqueous solution at 0° C. The solution was filtered through a pad of Celite, and the filtrate was extracted three times with a 5 ml portion of diethyl ether. The combined organic layer was washed with brine, dried over magnesium sulfate and evaporated under reduced pressure to obtain the titled compound.

IR (neat): 3450, 2970, 2360, 1740, 1460, 1260, 850, 760 cm$^{-1}$

Z-isomer: $^1$H-NMR (CDCl$_3$) δ: 0.20 (s, 9H), 0.92 (t, J=7.5 Hz, 3H), 0.93 (t, J=7.3 Hz, 3H), 1.38 (m, 2H), 1.64 (m, 2H), 2.01 (m, 2H), 2.29 (dd, J=8.2, 14.1 Hz, 1H), 2.50 (dd, J=3.9, 14.1 Hz, 1H), 2.78 (d, J=6.3 Hz, 1H), 4.16 (t, J=6.6 Hz, 2H), 4.35 (ddd, J=3.9, 6.3, 8.2 Hz, 1H), 4.57 (t, J=6.9 Hz, 1H) $^{13}$C-NMR (CDCl$_3$) δ: 0.6, 13.7, 14.4, 18.9, 19.2, 30.7, 42.1, 65.4, 68.8, 114.5, 144.8, 174.4

E-isomer: $^1$H-NMR (CDCl$_3$) δ: 2.95 (d, J=6.9 Hz, 1H), 4.76 (t, J=7.2 Hz, 1H) $^{13}$C-NMR (CDCl$_3$) δ: 0.3, 14.2, 15.3, 19.2, 20.3, 30.7, 35.8, 65.4, 68.9, 112.3, 146.2, 174.5

(2) n-Butyl 2-Hydroxy-4-oxoheptanoate:

In 2 ml of methanol was dissolved 25 mg of the silylenol ether obtained in (1) above, and the solution was poured into 10% hydrochloric acid-methanol cooled to 0° C. The solution was filtered through Celite, and the filtrate was extracted three times with a 5 ml portion of diethyl ether. The organic layer combined was washed with a saturated sodium chloride aqueous solution and dried over magnesium sulfate. The solvent was removed by distillation, and the residue was purified by silica gel column chromatography (eluent: hexane/ethyl acetate=15/1 by volume) to obtain 143 mg (yield 67%) of n-butyl 2-hydroxy-4-oxoheptanoate.

$[α]_D^{25}$: +5.9° (c=1.0, CHCl$_3$) (99% ee) IR (neat): 3470, 2970, 1720, 1460, 1260, 760 cm$^{-1}$ $^1$H-NMR (CDCl$_3$) δ: 0.91 (t, J=7.4 Hz, 3H), 0.92 (t, J=7.3 Hz, 3H), 1.37 (m, 3H), 1.61 (m, 2H), 1.62 (m, 2H), 2.42 (q, J=7.3 Hz, 2H), 2.67 (br, 1H), 2.85 (dd, J=6.0, 17.3 Hz, 1H), 2.93 (dd, J=4.5, 17.3 Hz, 1H), 4.18 (t, J=6.7 Hz, 2H), 4.45 (dd, J=4.5, 6.0 Hz, 1H) $^{13}$C-NMR (CDCl$_3$) δ: 13.7, 17.0, 19.1, 30.6, 45.4, 46.0, 65.8, 67.1, 173.9, 208.5

(R)-MTPA Ester: $^1$H-NMR (CDCl$_3$) δ: 0.83 (t, J=7.2 Hz, 3H), 0.93 (t, J=7.2 Hz, 3H), 1.31 (m, 2H), 1.52 (m, 2H), 1.66 (m, 2H), 2.28 (t, J=6.7 Hz, 2H), 2.91 (dd, J=3.7, 17.1 Hz, 1H), 2.99 (dd, J=8.2, 17.1 Hz, 1H), 3.64 (s, 3H), 4.21 (t, J=6.6 Hz, 2H), 5.77 (dd, J=3.7, 8.2 Hz, 1H)

(S)-MTPA Ester: $^1$H-NMR (CDCl$_3$) δ: 0.89 (t, J=7.3 Hz, 3H), 0.94 (t, J=7.2 Hz, 3H), 1.35 (m, 2H), 1.61 (m, 2H), 1.65 (m, 2H), 2.41 (t, J=6.7 Hz, 2H), 2.93 (dd, J=4.7, 17.3 Hz, 1H), 2.95 (dd, J=7.7, 17.3 Hz, 1H), 3.53 (s, 3H), 4.17 (t, J=6.7 Hz, 2H), 5.72 (dd, J=4.7, 7.7 Hz, 1H)

EXAMPLE 4

0.5 ml (0.1 mmol) of (R)-1 solution prepared in the same manner as in Example 1 were cooled to 0° C., and 190 mg (1 mmol) of (E)-1-ethylthio-1-trimethylsilyloxy-1-propene (77% E) and subsequently 130 mg (1 mmol) of freshly distilled butyl glyoxylate and 0.5 ml of toluene were added thereto, followed by allowing the mixture to react at 0° C. for 0.5 hour. The resulting mixture was poured into 10% hydrochloric acid-methanol cooled at 0° C. The solution was filtered through a pad of Celite, and the filtrate was extracted three times with a 5 ml portion of diethyl ether. The combined organic layer was washed with a saturated sodium chloride aqueous solution, dried over magnesium sulfate and evaporated under reduced pressure to remove the solvent. The residue was purified by silica gel column chromatography (eluent: hexane/ethyl acetate=15/1 by volume) to obtain 158 mg (yield 64%) of n-butyl 4-ethylthio-2-hydroxy-3-methyl-4-oxobutyrate.

$[α]_D^{26}$: +5.0° (c=1.0, CHCl$_3$) (>98% syn; >99% ee) IR (neat): 3500, 2970, 1730, 1460, 1260, 760 cm$^{-1}$ Syn-isomer: $^1$H-NMR (CDCl$_3$) δ: 0.94 (t, J=7.4 Hz, 3H), 1.23 (d, J=7.2 Hz, 3H), 1.27 (t, J=7.5 Hz, 3H), 1.39 (m, 2H), 1.66 (m, 2H), 2.91 (q, J=7.5 Hz, 2H), 3.06 (dq, J=3.6, 7.2 Hz, 1H), 3.19 (br, 1H), 4.22 (t, J=6.7 Hz, 2H), 4.59 (d, J=3.6 Hz, 1H) $^{13}$C-NMR (CDCl$_3$) δ: 11.5, 13.7, 14.6, 19.1, 23.5, 30.6, 51.3, 71.6, 173.2, 200.9

Anti-isomer: $^1$H-NMR (CDCl$_3$) δ: 0.94 (t, J=7.4 Hz, 3H), 1.35 (d, J=7.3 Hz, 3H), 1.38 (m, 2H), 1.67 (m, 2H), 2.08 (d, J=7.5 Hz, 2H), 3.12 (m, 1H), 3.35 (br, 1H), 4.18 (m, 2H), 4.25 (m, 1H) $^{13}$C-NMR (CDCl$_3$) δ: 14.1, 23.4, 51.2, 65.8, 72.8, 173.1, 200.7

EXAMPLE 5

An (S)-binaphthol-dichlorotitanium complex solution was prepared in the same manner as the preparation of the (R)-binaphthol-dichlorotitanium complex solution in Example 1 except that (S)-binaphthol was used in place of (R)-binaphthol. 0.5 ml (0.1 mmol) of the (S)-binaphtholdichlorotitanium complex solution were cooled to 0° C., and 218 mg (1 mmol) of (E)-1-t-butylthio-1-trimethylsilyloxy-1-propene (93% E) and subsequently 88 mg (1 mmol) of freshly distilled methyl glyoxylate and 0.5 ml of toluene were added thereto, followed by allowing the mixture to react at 0° C. for 2 hours. The resulting mixture was poured into 10% hydrochloric acid-methanol cooled at 0° C. The solution was filtered through a pad of Celite, and the filtrate was extracted three times with a 5 ml portion of diethyl ether. The combined organic layer was washed with a saturated sodium chloride aqueous solution, dried over magnesium sulfate, and evaporated under reduced pressure to remove the solvent. The residue was purified by silica gel column chromatography (eluent: hexane/ethyl acetate=15/1 by volume) to obtain mg of methyl 4-t-butylthio-2-hydroxy-3-methyl-4-oxobutyrate in a yield of 80% (16% syn, 84% ee; 84% anti, 93% ee).

IR (neat): 3500, 2970, 1720, 1460, 1260, 1190, 760 cm$^{-1}$

Syn-isomer: $^1$H-NMR (CDCl$_3$) δ: 1.30 (d, J=7.2 Hz, 3H), 1.45 (s, 9H), 3.02 (dq, J=4.4, 7.2 Hz, 1H), 3.12 (br, 1H), 3.79 (s, 3H), 4.23 (d, J=4.4 Hz, 1H) $^{13}$C-NMR (CDCl$_3$) δ: 14.1, 29.8, 48.5, 51.5, 52.6, 73.1, 173.5, 201.9

Anti-isomer: $^1$H-NMR (CDCl$_3$) δ: 1.20 (d, J=7.1 Hz, 3H), 1.47 (s, 9H), 2.97 (m, 1H), 3.80 (s, 3H), 4.54 (d, J=4.1 Hz, 1H) $^{13}$C-NMR (CDCl$_3$) δ: 11.9, 51.7, 52.8, 71.8

EXAMPLES 6 to 28

Examples 8, 10, 12, 15 to 25 and 28 were carried out in the same manner as in Example 1, and Examples 6, 7, 9, 11, 13, 14, 26 and 27 were carried out in the same manner as in Example 2, except for changing the reaction substrates and the solvent as shown in Table below. The intermediate products obtained and the reaction results are shown in the Table.

Analytical results of some of the products are shown below.

EXAMPLE 6

(1) syn-Methyl 2-hydroxy-3-methyl-4-(trimethylsilyl)oxy-4-hexenoate (intermediate):

IR (neat): 3510, 2960, 1740, 1460, 1260, 1060, 840, 760 cm$^{-1}$

Z-isomer: $^1$H-NMR (CDCl$_3$) δ: 0.22 (s, 9H), 0.95 (d, J=6.9 Hz, 3H), 1.57 (d, J=6.9 Hz, 3H), 2.53 (dq, J=3.0, 6.9 Hz, 1H), 2.63 (d, J=5.3 Hz, 1H), 3.79 (s, 3H), 4.08 (dd, J=3.0, 5.3 Hz, 1H), 4.67 (q, J=6.9 Hz, 1H) $^{13}$C-NMR (CDCl$_3$) δ: 0.7, 11.3, 15.3, 43.5, 52.5, 71.6, 103.6, 150.9, 174.8

E-isomer: $^1$H-NMR (CDCl$_3$) δ: 1.52 (d, J=6.8 Hz, 3H), 3.76 (s, 3H), 4.23 (m, 1H), 4.56 (m, 1H)

Methyl 2-Hydroxy-3-methyl-4-oxohexanoate:

[α]$_D^{26}$: +10.5° (c=1.1, CHCl$_3$) (98% syn; 98% ee) IR (neat): 3510, 2960, 1720, 1260, 740 cm$^{-1}$ HRMS for C$_8$H$_{14}$O$_4$: Calcd.: 174.0892; found: 174.0886

Syn-isomer: $^1$H-NMR (CDCl$_3$) δ: 1.05 (t, J=7.3 Hz, 3H), 1.15 (d, J=7.2 Hz, 3H), 2.55 (q, J=7.3 Hz, 2H), 2.94 (qd, J=3.8, 7.2 Hz, 1H), 3.12 (br, 1H), 3.79 (s, 3H), 4.56 (d, J=3.8 Hz, 1H) $^{13}$C-NMR (CDCl$_3$) δ: 8.0, 11.5, 34.8, 49.6, 53.8, 71.8, 174.4, 212.6

Anti-isomer: $^1$H-NMR (CDCl$_3$) δ: 1.02 (t, J=7.2 Hz, 3H), 1.26 (d, J=7.4 Hz, 3H), 2.49 (q, J=7.2 Hz, 2H), 3.02 (qd, J=4.5, 7.4 Hz, 1H), 3.28 (br, 1H), 3.75 (s, 3H), 4.21 (d, J=4.5 Hz, 1H) $^{13}$C-NMR (CDCl$_3$) δ: 8.0, 13.9, 35.3, 49.4, 51.3, 73.5, 174.3, 212.6

(R)-MTPA Ester of syn-isomer: $^1$H-NMR (CDCl$_3$) δ: 0.97 (t, J=7.4 Hz, 3H), 1.14 (d, J=7.2 Hz, 3H), 2.40 (q, J=7.2 Hz, 2H), 3.06 (m, 1H), 3.63 (s, 3H), 3.79 (s, 3H), 5.76 (d, J=4.5 Hz, 1H)

(S)-MTPA Ester of syn-isomer: $^1$H-NMR (CDCl$_3$) δ: 1.06 (t, J=7.2 Hz, 3H), 1.19 (d, J=7.2Hz, 3H), 2.52 (q, J=7.2 Hz, 2H), 3.13 (m, 1H), 3.54 (s, 3H), 3.76 (s, 3H), 5.74 (d, J=4.0 Hz, 1H)

EXAMPLE 7 syn-Methyl 2-Hydroxy-3-methyl-4-(t-butyldimethylsilyl)oxy-4-hexenoate (intermediate):

IR (neat): 3500, 2960, 1740, 1260, 840, 780 cm$^{-1}$

Z-isomer: $^1$H-NMR (CDCl$_3$) δ: 0.15 (s, 6H), 0.91 (d, J=4.8 Hz, 3H), 0.96 (s, 9H), 1.57 (d, J=6.8 Hz, 3H), 2.55 (m, 1H), 2.72 (br, 1H), 3.79 (s, 3H), 4.55 (m, 1H), 4.64 (q, J=6.8 Hz, 1H) $^{13}$C-NMR (CDCl$_3$) δ: −3.8, 11.1, 15.1, 18.4, 25.9, 43.2, 52.6, 71.6, 103.4, 150.7, 174.9

E-isomer: $^1$H-NMR (CDCl$_3$) δ: 3.74 (s, 3H), 4.26 (m, 1H), 4.51 (q, J=6.9Hz, 1H) −C-NMR (CDCl$_3$) δ: −3.6, 11.0, 15.13, 18.3, 25.7, 38.9, 52.1, 73.0, 103.9, 159.3, 174.8

EXAMPLE 9

S-Ethyl 4-Benzyloxy-3-hydroxy-2-methylbutanethioate:

[α]$_D^{26}$: −3° (c=1.0, CHCl$_3$) (72% syn; 90% ee) IR (neat): 3460, 2940, 1680, 1460, 1270, 1100, 960, 750 cm$^{-1}$ HRMS for C$_{14}$H$_{20}$O$_3$S: Calcd.: 268.1132; found: 268.1103

Syn-Isomer $^1$H-NMR (CDCl$_3$) δ: 1.23 (t, J=7.2 Hz, 3H), 1.25 (d, J=7.2 Hz, 3H), 2.48 (br, 1H), 2.81 (m, 1H), 2.85 (q, J=7.2 Hz, 2H), 3.47 (m, 2H), 4.04 (dt, J=4.4, 5.9 Hz, 1H), 4.53 (s, 2H), 7.25–7.38 (m, 5H) −C-NMR (CDCl$_3$) δ: 13.1, 14.5, 23.2, 50.8, 71.2, 71.6, 73.5, 127.9, 128.6, 137.8, 203.1

Anti-isomer: $^1$H-NMR (CDCl$_3$) δ: 1.18 (t, J=7.3 Hz, 3H), 1.19 (d, J=7.2 Hz, 3H), 2.48 (br, 1H), 2.83 (m, 1H), 2.89 (q, J=7.3 Hz, 2H), 3.49 (m, 2H), 3.94 (dt, J=4.1, 6.1 Hz, 1H), 4.56 (s, 2H), 7.25–7.39 (m, 5H) $^{13}$C-NMR (CDCl$_3$) δ: 14.5, 15.2, 23.2, 50.7, 71.8, 72.6, 75.3, 127.9, 128.5, 137.7, 203.3

(R)-MTPA Ester of syn-isomer: $^1$H-NMR (C$_6$D$_6$) δ: 0.93 (t, J=7.4 Hz, 3H), 1.01 (d, J=7.1 Hz, 3H), 2.57 3.26 (m, 1H), 3.51 (m, 2H), 3.54 (q, J=7.4 Hz, 2H), 3.26 (m, 1H), 3.51 (m, 2H), 3.54 (s, 3H), 4.15 (d, J=12.6 Hz, 1H), 4.22 (d, J=12.6 Hz, 1H), 5.80 (m, 1H), 7.03–7.21 (m, 10H) (S)-MTPA Ester of syn-isomer:. $^1$H-NMR (C$_6$D$_6$) δ: 0.96 (t, J=7.4 Hz, 3H), 1.07 (d, J=7.2 Hz, 3H), 2.61 (q, J=7.4 Hz, 2H), 3.33 (m, 1H), 3.53 (m, 2H), 3.54 (s, 3H), 4.07 (d, J=12.6 Hz, 1H), 4.16 (d, J=12.6 Hz, 1H), 5.87 (m, 1H), 7.00–7.21 (m, 10H)

(R)-MTPA Ester of anti-isomer: $^1$H-NMR (C$_6$D$_6$) δ: 0.88 (t, J=7.5 Hz, 3H), 1.07 (d, J=7.2 Hz, 3H), 2.52 (q, J=7.5 Hz, 2H), 3.20 (m, 1H), 3.30 (m, 2H), 3.51 (s, 3H), 4.11 (s, J=12.6 Hz, 1H), 4.18 (s, J=12.6 Hz, (1H), 5.67 (m, 1H), 7.00–7.22 (m, 10H)

(S)MTPA Ester of anti-isomer: $^1$H-NMR (C$_6$D$_6$) δ: 0.90 (t, J=7.4 Hz, 3H), 1.13 (d, J=7.2 Hz, 3H), 2.53 (q, J=7.4 Hz, 2H), 3.22 (m, 1H), 3.33 (m, 2H), 3.51 (s, 3H), 4.00 (d, J=12.6 Hz, 1H), 4.07 (d, J=12.0 Hz, 1H), 5.67 (m, 1H), 7.00–7.22 (m, 10H)

EXAMPLE 10

S-t-Butyl 3-Carbobutoxy-3-hydroxy-2-methylpropanethioate:

[α]$_D^{26}$: +9.5° (c=1.0, CHCl$_3$) (80% anti, 86% ee) IR (neat): 3500, 2960, 1740, 1680, 1460, 1260, 1200, 760 cm$^{-1}$ HRMS for C$_{13}$H$_{24}$O$_4$S: Calcd.: 276.1393; found: 276.1372

Syn-isomer: $^1$H-NMR (CDCl$_3$) δ: 0.94 (t, J=7.3 Hz, 3H), 1.19 (d, J=7.0 Hz, 3H), 1.37 (m, 2H), 1.47 (s, 9H), 1.63 (m, 2H), 2.97 (dq, J=3.8, 7.0 Hz, 1H), 3.07 (d, J=5.0 Hz, 1H), 4.21 (m, 2H), 4.54 (dd, J=3.8, 5.0 Hz, 1H) $^{13}$C-NMR (CDCl$_3$) δ: 11.8, 13.8, 19.2, 29.9, 30.7, 48.5, 51.7, 66.0, 71.6, 173.4, 202.0

Anti-isomer: $^1$H-NMR (CDCl$_3$) δ: 0.94 (t, J=7.3 Hz, 3H), 1.30 (d, J=7.2 Hz, 3H), 1.38 (m, 2H), 1.44 (s, 9H), 1.66 (m, 2H), 3.04 (dq, J=4.3, 7.2 Hz, 1H), 3.14 (d, J=8.0 Hz, 1H), 4.20 (m, 2H), 4.23 (m, 1H) $^{13}$C-NMR (CDCl$_3$) δ: 13.8, 14.3, 19.2, 29.9, 30.7, 48.6, 51.6, 65.8, 73.0, 173.5, 201.9

(R)-MTPA Ester of syn-isomer: $^1$H-NMR (CDCl$_3$) δ: 0.92 (t, J=7.3 Hz, 3H), 1.23 (d, J=7.4 Hz, 3H), 1.39 (m, 2H), 1.40 (s, 9H), 1.62 (m, 2H), 3.17 (m, 1H), 3.61 (s, 3H), 4.15 (t, J=6.7 Hz, 2H), 5.72 (d, J=3.9 Hz, 1H), 7.41 (m, 5H) (S)-MTPA Ester of syn-isomer: $^1$H-NMR (CDCl$_3$) δ: 0.90 (t, J=7.4 Hz, 3H), 1.25 (d, J=7.4 Hz, 3H), 1.35 (m, 2H), 1.44 (s, 9H), 1.62 (m, 2H), 3.19 (m, 1H), 3.62 (s, 3H), 4.13 (t, J=6.6 Hz, 2H), 5.75 (d, J=3.3 Hz, 1H), 7.41 (m, 5H)

(R)-MTPA Ester of anti-isomer: $^1$H-NMR (CDCl$_3$) δ: 0.91 (t, J=7.4 Hz, 3H), 1.20 (d, J=7.3 Hz, 3H), 1.37 (s, 9H), 1.38 (m, 2H), 1.63 (m, 2H), 3.13 (m, 1H), 3.62 (s, 3H), 4.23 (t, J=7.6 Hz, 2H), 5.28 (d, J=7.2 Hz, 1H), 7.41 (m, 5H) (S)-MTPA Ester of anti-isomer: $^1$H-NMR (CDCl$_3$) δ: 0.90 (t, J=7.4 Hz, 3H), 1.25 (d, J=7.4 Hz, 3H), 1.34 (m, 2H), 1.42 (s, 9H), 1.61 (m, 2H), 3.16 (m, 1H), 3.62 (s, 3H), 4.18 (t, J=6.6Hz, 2H), 5.29 (d, J=7.9 Hz, 1H), 7.41 (m, 5H)

EXAMPLE 11

S-t-Butyl 4-Benzyloxy-3-hydroxy-2-methylbutanethioate:

$[α]_D^{26}$: +10.3° (c=1.0, CHCl$_3$) (92% anti, 90% ee) IR (neat): 3430, 2960, 1680, 1460, 1270, 1070, 960, 740 cm$^{-1}$ HRMS for C$_{16}$H$_{24}$O$_3$S: Calcd.: 296.1449; found: 296.1447

Syn-isomer: $^1$H-NMR (CDCl$_3$) δ: 1.22 (d, J=7.1 Hz, 3H), 1.44 (s, 9H), 2.76 (m, 1H), 3.14 (br, 1H), 3.57 (m, 2H), 4.02 (m, 1H), 4.50 (d, J=12.3 Hz, 1H), 4.56 (d, J=12.3 Hz, 1H), 7.34 (m, 5H) $^{13}$C-NMR (CDCl$_3$) δ: 72.6, 73.8, 75.4, 128.1, 128.8

Anti-isomer: $^1$H-NMR (CDCl$_3$) δ: 1.16 (d, J=7.1 Hz, 3H), 1.46 (s, 9H), 2.80 (dt, J=4.4, 7.1 Hz, 1H), 2.83 (bs, 1H), 3.48 (dd, J=6.0, 9.7 Hz, 1H), 3.53 (dd, J=4.3, 9.7 Hz, 1H), 3.90 (ddd, J=4.3, 4.4, 6.0 Hz, 1H), 4.52 (d, J=11.9 Hz, 1H), 4.58 (d, J=11.9 Hz, 1H), 7.35 (m, 5H) $^{13}$C-NMR (CDCl$_3$) δ: 14.7, 29.7, 48.3, 50.4, 71.9, 72.7, 73.5, 128.0, 128.6, 136.9, 204.4

(R)-MTPA Ester of anti-isomer: $^1$H-NMR (CDCl$_3$) δ: 1.13 (d, J=7.2 Hz, 3H), 1.38 (s, 9H), 3.14 (m, 1H), 3.53 (s, 3H), 3.65 (dd, J=5.0, 11.3 Hz, 1H), 3.75 (dd, J=2.4, 11.3 Hz, 1H), 4.46 (d, J=11.9 Hz, 1H), 4.58 (d, J=11.9 Hz, 1H), 5.52 (ddd, J=2.4, 5.0, 7.8 Hz, 1H), 7.24–7.40 (m, 10H)

(S)-MTPA Ester of anti-isomer: $^1$H-NMR (CDCl$_3$) δ: 1.18 (d, J=7.1 Hz, 3H), 1.42 (s, 9H), 3.15 (qd, J=7.1, 8.8 Hz, 1H), 3.50 (s, 3H), 3.60 (dd, J=4.7, 11.5 Hz, 1H), 3.65 (dd, J=2.8, 11.5 Hz, 1H), 4.29 (d, J=12.1 Hz, 1H), 4.42 (d, J=12.1 Hz, 1H), 5.50 (ddd, J=2.8, 4.7, 8.8 Hz, 1H), 7.18–7.37 (m, 10H)

EXAMPLE 12

S-Ethyl 3-Carbobutoxy-3-hydroxy-2-methylpropanethioate:

$[α]_D^{26}$ −3.6° (c=1.0, CHCl$_3$) (92% syn; 98% ee) IR (neat): 3500, 2970, 1730, 1680, 1460, 1270, 1210, 970, 740 cm$^{-1}$ HRMS for C$_{11}$H$_{20}$O$_4$S: Calcd.: 248.1080; found: 248.1075

Syn-isomer: $^1$H-NMR (CDCl$_3$) δ: 0.95 (t, J=7.4 Hz, 3H), 1.24 (d, J=7.4 Hz, 3H), 1.26 (t, J=7.5 Hz, 3H), 1.37 (m, 2H), 1.62 (m, 2H), 2.91 (q, J=7.5 Hz, 2H), 3.07 (m, 2H), 4.22 (t, J=6.6 Hz, 2H), 4.59 (dd, J=3.8, 5.0 Hz, 1H) $^{13}$C-NMR (CDCl$_3$) δ: 11.5, 13.7, 14.6, 19.1, 23.5, 30.6, 51.3, 66.1, 71.6, 173.3, 200.9

Anti-isomer: $^1$H-NMR (CDCl$_3$) δ: 0.94 (t, J=7.4 Hz, 3H), 1.23 (t, J=7.4 Hz, 3H), 1.35 (d, J=7.3Hz, 3H), 1.37 (m, 2H), 1.62 (m, 2H), 2.87 (q, J=7.4 Hz, 2H), 3.13 (m, 2H), 4.18 (m, 2H), 4.26 (m, 1H) $^{13}$C-NMR (CDCl$_3$) δ: 13.7, 14.0, 14.6, 19.1, 23.4, 30.6, 51.2, 65.8, 72.8, 173.1, 200.6

(R)-MTPA Ester of syn-isomer: $^1$H-NMR (CDCl$_3$) δ: 0.92 (t, J=7.3 Hz, 3H), 1.18 (t, J=7.4 Hz, 3H), 1.26 (d, J=7.4 Hz, 3H), 1.38 (m, 2H), 1.65 (m, 2H), 2.81 (q, J=7.4 Hz, 2H), 3.12 (m, 2H), 3.63 (s, 3H), 4.22 (t, J=6.7 Hz, 2H), 5.77 (d, J=3.8 Hz, 1H), 7.43 (m, 5H)

(S)-MTPA Ester of syn-isomer: $^1$H-NMR (CDCl$_3$) δ: 0.90 (t, J=7.3 Hz, 3H), 1.26 (t, J=7.4 Hz, 3H), 1.30 (d, J=7.5 Hz, 3H), 1.36 (m, 2H), 1.64 (m, 2H), 2.92 (q, J=7.4 Hz, 2H), 3.26 (m, 1H), 3.64 (s, 3H), 4.20 (t, J=6.6 Hz, 2H), 5.78 (d, J=6.0 Hz, 1H), 7.45 (m, 5H)

EXAMPLE 16-1

S-Ethyl 4-Benzyloxy-3-hydroxybutanethionate:

To a solution of 21.5 mg (0.05 mmol) of (R)-1 in 3 ml of toluene were added 176 mg (1 mmol) of 1-ethylthio-1-(trimethylsilyl)oxyethene and 150 mg (1 mmol) of α-benzyloxyacetaldehyde at 0° C. After stirring for 2 hours at that temperature, the resultant mixture was poured into 10 ml of a buffer (pH 7) at 0° C. The solution was filtered through a pad of Celite, and the filtrate was extracted three times with a 5 ml portion of diethyl ether. The combined organic layer was washed with brine, dried over magnesium sulfate, and evaporated under reduced pressure to give a crude product in a silylated form. The crude product was poured into 10% hydrochloric acid-methanol, and the mixture was purified by silica gel chromatography (eluent: hexane/ethyl acetate=20/1 by volume) to obtain S-ethyl 4-benzyloxy-3-hydroxybutanethioate in a yield of 84%.

$[α]_D^{26}$: +11.4° (c=1.0, CHCl$_3$) (94% ee) IR (neat): 3560, 2870, 1690, 1460, 1270, 960, 740 cm$^{-1}$ HRMS for C$_{13}$H$_{18}$O$_3$S: Calcd.: 254.0975; found: 254.0952 $^1$H-NMR (CDCl$_3$) δ: 1.24 (t, J=7.4 Hz, 3H), 2.74 (dd, J=1.0, 11.3 Hz, 1H), 2.79 (dd, J=3.6, 11.3 Hz, 1H), 2.89 (q, J=7.4 Hz, 2H), 3.07 (br, 1H), 3.45 (dd, J=6.0, 9.6 Hz, 1H), 3.51 (dd, J=6.0, 9.6 Hz, 1H), 4.27 (m, 1H), 4.56 (s, 2H), 7.34 (m, 5H) $^{13}$C-NMR (CDCl$_3$) δ: 14.7, 23.5, 47.4, 67.7, 73.1, 73.7, 127.8, 128.5, 137.8, 198.4

(R)-MTPA Ester: $^1$H-NMR (CDCl$_3$) δ: 1.19 (t, J=7.4 Hz, 3H), 2.82 (q, J=7.4 Hz, 2H), 2.85 (dd, J=5.4, 17.2 Hz, 1H), 2.98 (dd, J=7.8, 17.2 Hz, 1H), 3.53 (s, 3H), 3.67 (dd, J=5.5, 11.6 Hz, 1H), 3.69 (dd, J=3.9, 11.6 Hz, 1H), 4.50 (d, J=11.9 Hz, 1H), 4.58 (d, J=11.9 Hz, 1H), 5.76 (m, 1H), 7.23–7.56 (m, 10H)

(S)-MTPA Ester: $^1$H-NMR (CDCl$_3$) δ: 1.23 (t, J=7.4 Hz, 3H), 2.87 (q, J=7.4 Hz, 2H), 2.94 (dd, J=4.7, 17.1 Hz, 1H), 3.04 (dd, J=8.2, 17.1 Hz, 1H), 3.51 (s, 3H), 3.57 (dd, J=4.9, 11.4 Hz, 1H), 3.59 (dd, J=5.3, 11.4 Hz, 1H), 4.40 (d, J=11.8 Hz, 1H), 4.45 (d, J=11.8 Hz, 1H), 5.76 (m, 1H), 7.23–7.55 (m, 10H)

EXAMPLE 17

S-Ethyl 3-Carbobutoxy-3-hydroxypropanethioate: $[α]_D^{26}$: +10.5° (c=1.0, CHCl$_3$) (95% ee) IR (neat): 3470, 2970, 1740, 1680, 1460, 1260, 1160, 970, 760 cm$^{-1}$ HRMS for C$_{10}$H$_{18}$O$_4$S: Calcd.: 234.0926; found: 234.0925 $^1$H-NMR (CDCl$_3$) δ: 0.94 (t, J=7.1 Hz, 3H), 1.26 (t, J=7.4 Hz, 3H), 1.39 (m, 2H), 1.65 (m, 2H), 2.91 (q, J=7.4 Hz, 2H), 2.98 (dd, J=6.3, 15.9 Hz, 1H), 3.07 (dd, J=4.3, 15.9 Hz, 1H), 3.10 (br, 1H), 4.21 (td, J=6.6, 14.3 Hz, 1H), 4.23 (td, J=6.7, 14.3 Hz, 1H), 4.51 (dd, J=4.3, 6.3 Hz, 1H) $^{13}$C-NMR (CDCl$_3$) δ: 13.7, 14.6, 19.1, 23.6, 30.5, 47.4, 66.1, 67.5, 173.5, 196.5 HPLC: tR of R-isomer: 13.9 min; tR of S-isomer: 16.2 min

EXAMPLE 19

S-t-Butyl 4-Benzyloxy-3-hydroxybutanethioate:

$[\alpha]_D^{26}$: +10.0° (c=1.0, CHCl$_3$) (96% ee) IR (neat): 3450, 2970, 1680, 1460, 1370, 1200, 1100, 740 cm$^{-1}$ $^1$H-NMR (CDCl$_3$) δ: 1.46 (s, 9H), 2.69 (m, 2H), 2.87 (d, J=4.1 Hz, 1H), 3.44 (dd, J=6.0, 9.6 Hz, 1H), 3.49 (dd, J=4.7, 9.6 Hz, 1H), 4.25 (m, 1H), 4.56 (s, 2H), 7.28–7.38 (m, 5H) $^{13}$C-NMR (CDCl$_3$) δ: 29.6, 47.7, 48.5 67.7, 73.1, 73.5, 127.9, 128.6, 137.4, 199.6

(R)-MTPA Ester: $^1$H-NMR (C$_6$D$_6$) δ: 1.31 (s, 9H), 2.37 (dd, J=4.8, 16.2 Hz, 1H), 2.70 (dd, J=8.1, 16.2 Hz, 1H), 3.25 (dd, J=6.0, 10.8 Hz, 1H), 3.28 (dd, J=3.6, 10.8 Hz, 1H), 3.51 (s, 3H), 4.12 (d, J=12.0 Hz, 1H), 4.21 (d, J=12.0 Hz, 1H), 5.83 (dddd, J=3.6, 4.8, 6.0, 8.1 Hz, 1H), 6.85–7.32 (m, 10H)

(S)MTPA Ester: $^1$H-NMR (C$_6$D$_6$) δ: 1.32 (s, 9H), 2.44 (dd, J=3.9, 16.5 Hz, 1H), 2.72 (dd, J=8.7, 16.5 Hz, 1H), 3.16 (dd, J=3.0, 11.1 Hz, 1H), 3.18 (dd, J=4.5, 11.1 Hz, 1H), 3.52 (s, 3H), 4.04 (d, J=12.3 Hz, 1H), 4.11 (d, J=12.3 Hz, 1H), 5.82 (m, 1 H), 6.87–7.26 (m, 10H)

EXAMPLE 20

S-t-Butyl 4-Chloro-3-hydroxybutanethioate:

$[\alpha]_D^{26}$: +23.0° (c=1.0, CHCl$_3$) (91% ee) IR (neat): 3430, 2970, 1680, 1460, 1370, 1160, 990 cm$^{-1}$ $^1$H-NMR (CDCl$_3$) δ: 1.47 (s, 9H), 2.72 (dd, J=5.5, 13.1 Hz, 1H), 2.79 (dd, J=6.6, 13.1 Hz, 1H), 3.01 (d, J=4.9 Hz, 1H), 3.54 (dd, J=5.5, 11.2 Hz, 1H), 3.60 (dd, J=4.9, 11.2 Hz, 1H), 4.25 (m, 1H) $^{13}$C-NMR (CDCl$_3$) δ: 29.7, 47.8, 48.3, 48.8, 68.5, 199.3

(R)-MTPA Ester: $^1$H-NMR (CDCl$_3$) δ: 1.41 (s, 9H), 2.87 (dd, J=5.4, 15.2 Hz, 1H), 2.95 (dd, J=7.5, 15.2 Hz, 1H), 3.57 (s, 3H), 3.71 (dd, J=4.8, 11.2 Hz, 1H), 3.87 (dd, J=4.2, 11.2 Hz, 1H), 5.68 (m, 1H), 7.40 (m, 5H)

(S)MTPA Ester: $^1$H-NMR (CDCl$_3$) δ: 1.46 (s, 9H), 2.93 (dd, J=5.4, 15.3 Hz, 1H), 3.00 (dd, J=8.1, 15.3 Hz, 1H), 3.54 (s, 3H), 3.65 (dd, J=4.8, 12.0 Hz, 1H), 3.73 (dd, J=5.1, 12.0 Hz, 1H), 5.67 (m, 1H), 7.40 (m, 5H)

EXAMPLE 21

4-Chloro-3-hydroxybutanethioate: $[\alpha]_D^{26}$: +23.0° (c=1.0, CHCl$_3$) (80% ee) IR (neat): 3410, 2970, 1680, 1470, 1370, 1270, 1200, 1050, 760 cm$^{-1}$ $^1$H-NMR (CDCl$_3$) δ: 1.27 (t, J=7.4Hz, 3H), 2.87 (d, J=6.4 Hz, 2H), 2.92 (q, J=7.4 Hz, 2H), 3.02 (bs, 1H), 3.57 (dd, J=5.6, 11.2 Hz, 1H), 3.62 (dd, J=5.0, 11.2 Hz, 1H), 4.30 (m, 1H) $^{13}$C-NMR (CDCl$_3$) δ: 14.5, 23.5, 47.5, 48.2, 68.3, 198.1

(R)-MTPA Ester: $^1$H-NMR (CDCl$_3$) δ: 1.20 (t, J=7.4 Hz, 3H), 2.83 (q, J=7.4 Hz, 2H), 2.92 (dd, J=5.6, 16.2 Hz, 1H), 3.03 (dd, J=7.3, 16.2 Hz, 1H), 3.58 (s, 3H), 3.73 (dd, J=4.9, 12.2 Hz, 1H), 3.87 (dd, J=4.1, 12.2 Hz, 1H), 5.70 (m, 1H), 7.40 (m, 5H)

(S)-MTPA Ester: $^1$H-NMR (CDCl$_3$) δ: 1.25 (t, J=7.4 Hz, 3H), 2.90 (q, J=7.4 Hz, 2H), 3.02 (dd, J=5.6, 16.2 Hz, 1H), 3.10 (dd, J=7.6, 16.2 Hz, 1H), 3.52 (s, 3H), 3.67 (dd, J=4.7, 12.0 Hz, 1H), 3.74 (dd, J=4.8, 12.0 Hz, 1H), 5.70 (m, 1H), 7.40 (m, 5H)

EXAMPLE 22

S-t-Butyl 3-Hydroxydodecanethioate:

$[\alpha]_D^{26}$: +15.0° (c=1.0, CHCl$_3$) (91% ee) IR (neat): 3470, 2930, 1670, 1460, 1370, 1270, 1160, 760 cm$^{-1}$ HRMS for C$_{15}$H$_{30}$O$_2$S: Calcd.: 274.1965; found: 274.1979 $^1$H-NMR (CDCl$_3$) δ: 0.87 (t, J=7.0 Hz, 3H), 1.26–1.45 (m, 14H), 1.47 (s, 9H), 2.54 (dd, J=8.4, 15.7 Hz, 1H), 2.63 (dd, J=3.3, 15.7 Hz, 1H), 2.78 (br, 1H), 3.99 (m, 1H) $^{13}$C-NMR (CDCl$_3$) δ: 14.2, 22.8, 25.6, 29.4, 29.5, 29.7, 29.9, 32.6, 36.6, 48.6, 51.0, 68.91, 200.6

(R)-MTPA Ester: $^1$H-NMR (C$_6$D$_6$) δ: 1.13 (t, J=7.3 Hz, 3H), 1.13–1.32 (m, 14H), 1.33 (s, 9H), 2.36 (dd, J=4.8, 15.7 Hz, 1H), 2.68 (dd, J=8.1, 15.7 Hz, 1H), 3.46 (s, 3H), 5.65 (m, 1H), 7.00–7.16 (m, 5H)

(S)-MTPA Ester: $^1$H-NMR (C$_6$D$_6$) δ: 1.10 (t, J=7.3 Hz, 3H), 1.10–1.30 (m, 14H), 1.36 (s, 9H), 2.34 (dd, J=3.8, 15.6 Hz, 1H), 2.63 (dd, J=8.1, 15.6 Hz, 1H), 3.55 (s, 3H), 5.65 (m, 1H), 6.07–7.15 (m, 5H)

EXAMPLE 23

S-Ethyl 3-Hydroxydodecanethioate:

$[\alpha]_D^{26}$: +15.2° (c=1.3, CHCl$_3$) (86% ee) IR (neat): 3450, 2930, 1680, 1460, 1260, 1050, 760 cm$^{-1}$ HRMS for C$_{13}$H$_{26}$O$_2$S: Calcd.: 246.1652; found: 246.1675 $^1$H-NMR (CDCl$_3$) δ: 0.88 (t, J=7.1 Hz, 3H), 1.26 (t, J=7.4 Hz, 3H), 1.28–1.43 (m, 14H), 2.70 (dd, J=8.3, 15.7Hz, 1H), 2.74 (dd, J=3.5, 15.7 Hz, 1H), 2.77 (bs, 1H), 2.90 (q, J=7.4 Hz, 2H), 4.04 (m, 1H) $^{13}$C-NMR (CDCl$_3$) δ: 14.2, 14.7, 25.5, 29.3, 29.6, 29.6, 31.9, 36.6, 50.7, 68.8, 199.8

(R)-MTPA Ester: $^1$H-NMR (C$_6$D$_6$) δ: 1.10 (t, J=7.4 Hz, 3H), 1.13 (t, J=7.3 Hz, 3H), 1.32–1.60 (m, 14H), 2.53 (dd, J=4.5, 16.3 Hz, 1H), 2.75 (q, J=7.4 Hz, 2H), 2.83 (dd, J=8.1, 16.3 Hz, 1H), 3.62 (s, 3H), 5.83 (m, 1H), 7.22–7.34 (m, 5H)

(S)-MTPA Ester: $^1$H-NMR (C$_6$D$_6$) δ: 1.08 (t, J=7.4 Hz, 3H), 1.15 (t, J=7.4 Hz, 3H), 1.21–1.52 (m, 14H), 2.55 (dd, J=3.9, 16.1Hz, 1H), 2.80 (q, J=7.4 Hz, 2H), 2.88 (dd, J=8.3, 16.1Hz, 1H), 3.67 (s, 3H), 5.83 (m, 1H), 7.11–7.30 (m, 5H)

EXAMPLE 24

S-Ethyl 3-Hydroxy-4-methylpentanethioate:

$[\alpha]_D^{26}$+36.8° (c=1.0, CHCl$_3$) (85% ee) IR (neat): 3450, 2970, 1670, 1460, 1270, 1050, 760 cm$^{-1}$ $^1$H-NMR (CDCl$_3$) δ: 0.92 (d, J=6.Hz, 3H), 0.94 (d, J=6.8 Hz, 3H), 1.26 (t, J=7.4 Hz, 3H), 1.72 (m, 1H), 2.63 (dd, J=8.9, 15.6 Hz, 1H), 2.73 (dd, J=3.2, 15.6 Hz, 1H), 2.77 (br, 1H), 2.91 (q, J=7.4 Hz, 2H), 3.83 (ddd, J=3.2, 5.6, 8.9 Hz, 1H) $^{13}$C-NMR (CDCl$_3$) δ: 14.8, 17.7, 18.5, 23.6, 33.3, 48.0, 73.4, 200.1

(R)-MTPA Ester: $^1$H-NMR (C$_6$D$_6$) δ: 0.82 (d, J=6.7 Hz, 3H), 0.85 (d, J=6.7 Hz, 3H), 1.13 (t, J=7.4 Hz, 3H), 1.89 (m, 1H), 2.54 (dd, J=3.0, 15.6 Hz, 1H), 2.77 (q, J=7.4 Hz, 2H), 2.82 (dd, J=7.7, 15.4 Hz, 1H), 3.60 (s, 3H), 5.77 (m, 1H), 7.16–7.33 m, 5H)

(S)-MTPA Ester: $^1$H-NMR (C$_6$D$_6$) δ: 0.72 (dd, J=6.7 Hz, 3H), 0.73 (d, J=6.7 Hz, 3H), 1.17 (t, J=7.5 Hz, 3H), 1.85 (m, 1H), 2.55 (dd, J=3.2, 15.6 Hz, 1H), 2.81 (q, J=7.5 Hz, 2H), 2.84 (dd, J=8.1, 15.6 Hz, 1H), 3.68 (s, 3H), 5.77 (m, 1H), 7.17–7.33 (m, 5H)

EXAMPLE 25

(4E)-S-Ethyl 3-Hydroxy-4-hexenoate:

$[\alpha]_D^{26}$: +7.9° (c=0.5, CHCl$_3$) (81% ee) IR (neat): 3470, 2950, 1670, 1450, 970, 820, 750 cm$^{-1}$ HRMS for C$_8$H$_{14}$O$_2$S: Calcd.: 174.0714; found: 174.0729 $^1$H-NMR (CDCl$_3$) δ: 1.25 (t, J=7.4 Hz, 3H), 1.68 (dd, J=1.6, 6.5 Hz, 3H), 2.65 (br, 1H), 2.73 (d, J=6.3 Hz, 2H), 2.88 (q, J=7.4 Hz, 2H), 4.50 (td, J=6.3, 6.7 Hz, 1H), 5.47 (ddd, J=1.6, 6.7, 16.6 Hz, 1H), 5.71 (qd, J=6.5, 16.6 Hz, 1H) $^{13}$C-NMR (CDCl$_3$) δ: 14.8, 17.8, 23.6, 50.8, 69.6, 127.0, 131.2, 203.1 HPLC: t$_R$ of R-isomer: 9.5 min; t$_R$ of S-isomer: 12.3 min

EXAMPLE 26

(1) Methyl 2-Hydroxy-4-(t-butyldimethylsilyl)oxy-4-pentenoate (intermediate):

IR (neat): 3510, 2950, 1740, 1460, 1260, 840, 790 cm$^{-1}$ $^1$H-NMR (CDCl$_3$) δ: 0.19 (s, 6H), 0.92 (s, 9H), 2.39 (dd, J=7.7, 14.0 Hz, 1H), 2.55 (dd, J=4.2, 14.0 Hz, 1H), 2.89 (d, J=6.4 Hz, 1H), 3.77 (s, 3H), 4.13 (s, 1H), 4.14 (s, 1H), 4.39 (ddd, J=4.2, 6.4, 7.7 Hz, 1) $^{13}$C-NMR (CDCl$_3$) δ: −3.8, 18.3, 25.9, 45.2, 52.6, 68.2, 92.7, 154.7, 174.5

(2) Methyl 2-Hydroxy-4-oxopentanoate:

[α]$_D^{26}$+4.3° CHCl$_3$) (>99% ee) IR (neat): 3500, 2960, 1730, 1250, 740 cm$^{-1}$ HRMS for C$_6$H$_{10}$O$_4$: Calcd.: 146.0579; found: 146.0587 $^1$H-NMR (CDCl$_3$) δ: 2.20 (s, 3H), 2.88 (m, 1H), 2.94 (bs, 1H), 3.02 (m, 1H), 3.77 (s, 3H), 4.48 (m, 1H) $^{13}$C-NMR (CDCl$_3$) δ: 30.7, 46.9, 52.9, 67.1, 174.9, 206.3

(3) (R)-MTPA Ester: $^1$H-NMR (CCDCl$_3$) δ: 2.08 (s, 3H), 3.03 (d, J=6.1 Hz, 2H), 3.63 (s, 3H), 3.78 (S, 3H), 5.75 (t, J=6.1 Hz, 1H)

(S)-MTPA Ester: $^1$H-NMR (CDCl$_3$) δ: 2.18 (s, 3H), 3.06 (d, J=6.1 Hz, 2H), 3.54 (s, 3H), 3.75 (s, 3H), 5.72 (t, J=6.1 Hz, 1H)

EXAMPLE 27

(1) Butyl 2-Hydroxy-4-(t-butyldimethylsilyl)oxy-4-pentenoate (intermediate):

IR (neat): 3510, 2960, 1740, 1460, 1260, 1200, 830, 790 cm$^{-1}$ $^1$H-NMR (CDCl$_3$) δ: 0.19 (s, 6H), 0.91 (t, J=7.4 Hz, 3H), 0.92 (s, 9H), 1.42 (m, 2H), 1.64 (m, 2H), 2.36 (dd, J=7.8, 14.2 Hz, 1H), 2.55 (dd, J=4.2, 14.2 Hz, 1H), 2.88 (d, j=6.3 Hz, 1H), 4.14 (s, 1H), 4.15 (s, 1H), 4.17 (t, J=6.7 Hz, 2H), 4.37 (ddd, J=4.2, 6.3, 7.1 Hz, 1H) $^{13}$C-NMR (CDCl$_3$) δ: −4.6, −3.5, 13.7, 18.3, 19.1, 25.7, 30.7, 41.9, 65.5, 68.7, 92.9, 154.7, 174.9

(2) Butyl 2-Hydroxy-4-oxopentanoate:

[α]$_D^{26}$: +2.7° (c=1.1, CHCl$_3$) (>99% ee) IR (neat): 3500, 2960, 1720, 1370, 1260, 740 cm$^{-1}$ HRMS for C$_9$H$_{16}$O$_4$: Calcd.: 188.1049; found: 188.1052 $^1$H (CDCl$_3$) δ0.92 (t, J=7.4 Hz, 3H), 1.37 (m, 2H), 1.62 (m, 2H), 2.19 (s, 3H), 2.87 (dd, J=6.0, 17.3 Hz, 1H), 2.96 (dd, J=4.1, 17.3 Hz, 1H), 3.21 (br, 1H), 4.18 (t, J=6.6 Hz, 2H), 4.46 (dd, J=4.1, 6.0 Hz, 1H) $^{13}$C-NMR (CDCl$_3$) δ: 13.7, 19.1, 30.5, 30.6, 46.9, 65.8, 67.0, 173.8, 206.1

(3)(R)-MTPA Ester: $^1$H-NMR (CCDCl$_3$) δ: 0.92 (t, J=7.2 Hz, 3H), 1.31 (m, 2H), 1.66 (m, 2H), 2.08 (s, 3H), 3.00 (m, 2H), 3.64 (s, 3H), 4.21 (t, J=6.6 Hz, 2H), 5.75 (dd, J=4.2, 7.8 Hz, 1H)

(S)-MTPA Ester: $^1$H-NMR (CDCl$_3$) δ: 0.91 (t, J=7.2 Hz, 3H), 1.30 (m, 2H), 1.64 (m, 2H), 2.19 (s, 3H), 3.05 (d, J=6.0 Hz, 2H), 3.50 (s, 3H), 4.15 (t, J=6.6 Hz, 2H), 5.69 (t, J=6.0 Hz, 1H) The following abbreviations are used in the following table.

Me: a methyl group
Et: an ethyl group
Bu: a butyl group
Ph: a phenyl group
Bn: a benzyl group
TMS: a trimethylsilyl group
TBS: a tert-butyldimethylsilyl

TABLE

| Example No. | Silyl-enol Ether | R$^5$CHO | Solvent | Intermediate | Yield (%) | Ratio of Syn (% ee) | Ratio of Anti (% ee) |
|---|---|---|---|---|---|---|---|
| 6 | OTMS (ethyl-substituted) | CHO–CO$_2$Me | toluene | OTMS OH –CO$_2$Me | 58 | 98 (98) | 2 |
| 7 | OTBS (ethyl-substituted) | CHO–CO$_2$Me | CH$_2$Cl$_2$ | OTBS OH –CO$_2$Me | 73 | 73 (77) | 27 |
| 8 | OTMS (ethyl-substituted) | CHO–CO$_2$Bu | CH$_2$Cl$_2$ |  | 64 | 98 (99) | 2 |
| 9 | OTMS, EtS | CHO–OBn | toluene | BnO OTMS O SEt | 80 | 72 (90) | 28 |
| 10 | OTMS, tBuS | CHO–CO$_2$Bu | toluene |  | 81 | 20 (69) | 80 (86) |
| 11 | OTMS, tBuS | CHO–OBn | toluene | BnO OTMS O StBu | 72 | 8 | 92 (90) |
| 12 | OTMS, EtS | CHO–CO$_2$Bu | toluene |  | 87 | 92 (98) | 8 (51) |
| 13 | OTMS, EtS | CHO–OBn | toluene | BnO OTMS O SEt | 85 | 72 (90) | 28 |

TABLE-continued

| Example No. | Silyl-enol Ether | R⁵CHO | Solvent | Intermediate | Yield (%) | Ratio of Syn (% ee) | Ratio of Anti (% ee) |
|---|---|---|---|---|---|---|---|
| 14 | OTMS, tBuS, (methyl) | CHO–CO₂Bu | toluene | OTMS O, BuO₂C–StBu | 57 | 57 (88) | 43 |
| 15 | OTMS, PhO, (methyl) | CHO–CO₂Bu | toluene | | 80 | 54 (90) | 46 (80) |
| 16-1 | OTMS, EtS | CHO–OBn | toluene | | 84 | (94% ee) | |
| 16-2 | OTMS, EtS | CHO–OBn | CH₂Cl₂ | | 71 | (91% ee) | |
| 16-3 | OTMS, EtS | CHO–OBn | nitroethane | | 91 | (85% ee) | |
| 17 | OTMS, EtS | CHO–CO₂Bu | toluene | | 89 | (95% ee) | |
| 18 | OTMS, PhO, (isopropyl) | CHO–CO₂Bu | toluene | | 71 | (80% ee) | |
| 19 | OTMS, tBuS | CHO–OBn | toluene | | 80 | (96% ee) | |
| 20 | OTMS, tBuS | CHO–Cl | toluene | | 61 | (91% ee) | |
| 20-1 | OTMS, tBuS | CHO–Cl | CH₂Cl₂ | | 60 | (81% ee) | |
| 21 | OTMS, EtS | CHO–Cl | CH₂Cl₂ | | 47 | (80% ee) | |
| 22 | OTMS, tBuS | CHO–(CH₂)₇CH₃ | toluene | | 60 | (91% ee) | |
| 23 | OTMS, EtS | CHO–(CH₂)₇CH₃ | toluene | | 67 | (86% ee) | |
| 23-1 | OTMS, EtS | CHO–(CH₂)₇CH₃ | CH₂Cl₂ | | 60 | (60% ee) | |
| 24 | OTMS, EtS | CHO–CH(CH₃)₂ | toluene | | 61 | (85% ee) | |
| 25 | OTMS, EtS | CHO–CH=CHCH₃ | toluene | | 60 | (81% ee) | |
| 26 | OTBS | CHO–CO₂Me | CH₂Cl₂ | OTBS OH, CO₂Me | 71 | (99% ee) | |

TABLE-continued

| Example No. | Silyl-enol Ether | R⁵CHO | Solvent | Intermediate | Yield (%) | Ratio of Syn (% ee) | Ratio of Anti (% ee) |
|---|---|---|---|---|---|---|---|
| 27 | 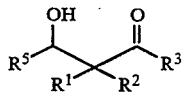 OTBS | CHO<br>\|<br>CO₂Bu | CH₂Cl₂ | 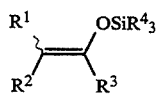 OTBS  OH<br>            CO₂Bu | 73 | | (99% ee) |
| 28 |  OTMS | CHO<br>L—OBn | CH₂Cl₂ | | 50 | | (89% ee) |

It can be seen from the above results that an optically active β-hydroxyketone can be obtained efficiently with high diastereo-selectivity and high enantio-selectivity by using the optically active binaphthol-titanium complex.

While the invention has been described in detail and with reference to specific examples thereof, it will be apparent to one skilled in the art that various changes and modifications can be made therein without departing from the spirit and scope thereof.

What is claimed is:

1. A process for producing an optically active β-hydroxyketone represented by formula (I):

$$R^5 \underset{\underset{R^1}{|}}{\overset{\underset{|}{OH}}{C}} - \underset{\underset{R^2}{|}}{C} - \overset{O}{\underset{}{C}} - R^3 \quad (I)$$

wherein $R^1$ and $R^2$, which may be the same or different, each represent a hydrogen atom or a lower alkyl group; $R^3$ represents a lower alkyl group, a lower alkyloxy group, a phenyloxy group or a lower alkylthio group; and $R^5$ represents an alkyl group having from 1 to 10 carbon atoms, a halogenated lower alkyl group, a lower alkenyl group, a benzyloxymethyl group or a lower alkyloxycarbonyl group, comprising reacting a silyl-enol ether represented by formula (II):

$$\underset{R^2}{\overset{R^1}{>}}=\underset{R^3}{\overset{OSiR^4_3}{<}} \quad (II)$$

wherein $R^1$, $R^2$, and $R^3$ are as defined above; and three $R^4$'s, which may be the same or different, each represent a lower alkyl group or a phenyl group, with a substituted aldehyde represented by formula (III):

$$R^5CHO \quad (III)$$

wherein $R^5$ is as defined above, in the presence of a binaphthol-titanium complex represented by formula (IV):

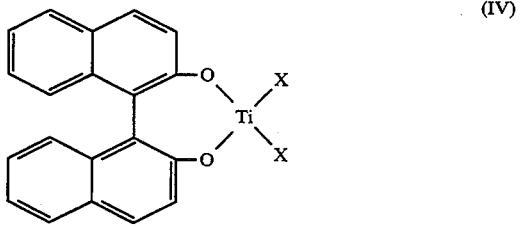

wherein X represents a chlorine atom or a bromine atom to thereby form a reaction product of said silyl-enol ether represented by formula (II) and said substituted aldehyde represented by formula (III) and then hydrolyzing the reaction product to obtain the optically active β-hydroxyketone represented by formula (I).

2. A process as claimed in claim 1, wherein the reacting is conducted in an organic solvent.

3. A process as claimed in claim 2, wherein the respective concentrations of the silyl-enol ether and the substituted aldehyde in the organic solvent are approximately from 0.1 to 5 mol/l.

4. A process as claimed in claim 1, wherein the binaphthol-titanium complex is present such that the amount of the binaphthol-titanium complex is approximately from 0.02 to 1 mol per mol of the respective amounts of the silyl-enol ether and the substituted aldehyde.

5. A process as claimed in claim 1, wherein the reacting is conducted at a temperature of approximately from −50° C. to 0° C.

6. The process of claim 1, wherein said hydrolyzing of the reaction product to obtain the optically active β-hydroxyketone represented by formula (I) is by acid.

* * * * *